(12) United States Patent
Tu et al.

(10) Patent No.: US 11,308,621 B2
(45) Date of Patent: Apr. 19, 2022

(54) METHOD AND APPARATUS FOR ACQUIRING BLOOD FLOW VOLUME AND BLOOD FLOW VELOCITY OF CORONARY ARTERY

(71) Applicant: PULSE MEDICAL IMAGING TECHNOLOGY (SHANGHAI) CO. LTD., Shanghai (CN)

(72) Inventors: Shengxian Tu, Shanghai (CN); Zehang Li, Shanghai (CN); Jingfeng Han, Shanghai (CN); Guanyu Li, Shanghai (CN)

(*) Notice: Subject to any disclaimer, the term of this patent is extended or adjusted under 35 U.S.C. 154(b) by 0 days.

(21) Appl. No.: 17/601,520

(22) PCT Filed: Apr. 15, 2019

(86) PCT No.: PCT/CN2019/082715
§ 371 (c)(1),
(2) Date: Oct. 5, 2021

(87) PCT Pub. No.: WO2020/210948
PCT Pub. Date: Oct. 22, 2020

(65) Prior Publication Data
US 2022/0092784 A1    Mar. 24, 2022

(51) Int. Cl.
*G06T 7/00* (2017.01)
*A61B 6/00* (2006.01)
(Continued)

(52) U.S. Cl.
CPC ............ *G06T 7/0014* (2013.01); *A61B 6/507* (2013.01); *A61B 6/5217* (2013.01); *G06T 7/62* (2017.01);
(Continued)

(58) Field of Classification Search
CPC . G06T 2207/30104; G06T 2207/10076; G06T 2210/41; G06T 7/246;
(Continued)

(56) References Cited

U.S. PATENT DOCUMENTS

2014/0222354 A1   8/2014  Krittian et al.
2017/0076467 A1   3/2017  Mistretta et al.
(Continued)

FOREIGN PATENT DOCUMENTS

CN   106714673 A   5/2017
CN   107689032 A   2/2018
CN   109907772 A   6/2019

OTHER PUBLICATIONS

International Search Report dated Sep. 27, for 2020 for corresponding PCT patent application No. PCT/CN2019/082715.

*Primary Examiner* — Manuchehr Rahmjoo
(74) *Attorney, Agent, or Firm* — Abelman, Frayne & Schwab; Stefan Knirr

(57) ABSTRACT

A method for acquiring a blood flow volume and a blood flow velocity of a coronary artery is provided. The method comprises: acquiring image information of a coronary artery to obtain geometrical feature data of the coronary artery; obtaining, according to the geometrical feature data of the coronary artery, the total volume V of a reference lumen of the coronary artery; and calculating a blood flow volume Q at coronary artery ostia according to the following formula:

$$Q = K * V^{\frac{3}{4}},$$

wherein when the unit of Q is mm³/s, and when the unit of V is mm³, a value range of K is 5-9.5. A blood flow volume and a blood flow velocity of a coronary artery are obtained (Continued)

by means of image information of the coronary artery. Compared with a method, in the prior art, for estimating a blood flow volume of a coronary artery by means of the size of a cardiac muscle, this method is simpler, and can provide a more accurate boundary condition for image-based hemodynamic calculation.

26 Claims, 3 Drawing Sheets

(51) Int. Cl.
  *G06T 7/62* (2017.01)
  *G06V 10/25* (2022.01)
  *G16H 50/30* (2018.01)
  *G16H 30/40* (2018.01)
  *A61B 6/03* (2006.01)

(52) U.S. Cl.
  CPC .............. *G06V 10/25* (2022.01); *G16H 30/40* (2018.01); *G16H 50/30* (2018.01); *A61B 6/032* (2013.01); *G06T 2207/10081* (2013.01); *G06T 2207/30048* (2013.01); *G06T 2207/30104* (2013.01); *G06V 2201/03* (2022.01)

(58) Field of Classification Search
  CPC .................. G06T 11/008; G06T 15/08; G06T 2207/10088; G06T 2207/10116; G06T 2207/20224; G06T 2207/30048; G06T 2211/404; G06T 7/0012; G06T 7/50; G06T 7/62; A61B 5/0013; A61B 5/004; A61B 5/0044; A61B 5/02; A61B 5/02014; A61B 5/021; A61B 5/026; A61B 5/055; A61B 5/4848; A61B 5/7271; A61B 5/7275; A61B 6/504; A61B 8/06; G06F 30/23; G06K 9/6267; G16H 50/30; G16H 50/50
  See application file for complete search history.

(56) References Cited

U.S. PATENT DOCUMENTS

2017/0347966 A1   12/2017  Yagi et al.
2021/0259559 A1*   8/2021  Tu ......................... G16H 30/40

* cited by examiner

METHOD AND APPARATUS FOR ACQUIRING BLOOD FLOW VOLUME AND BLOOD FLOW VELOCITY OF CORONARY ARTERY

CROSS REFERENCE TO RELATED APPLICATIONS

This application is a national phase of PCT application No. PCT/CN2019/082715, filed Apr. 4, 2019, which is incorporated herein by reference thereto.

TECHNICAL FIELD

The present invention relates to the field of medical technology, and specifically relates to a method and apparatus for acquiring a blood flow volume and a blood flow velocity of a coronary artery.

BACKGROUND

The World Health Organization report shows that cardiovascular diseases have become a greatest threat to human health. In order to better understand the physiological and pathological behaviors of cardiovascular diseases, an in-depth study of an arterial blood flow has become a primary task of hemodynamics.

Wherein, a blood flow volume and a blood flow velocity of a coronary artery are important parameters for hemodynamic calculations. Current methods for calculating the blood flow volume and the blood flow velocity of the coronary artery are mainly divided into invasive methods and non-invasive methods.

The invasive methods include a coronary angiography thrombolysis in myocardial infarction (TIMI) frame count method. Since information of blood flow changing over time can be seen by means of coronary angiography, a blood flow velocity of a current blood vessel can be calculated by means of a length of a blood vessel segment and the time that blood flows through the blood vessel segment.

The non-invasive methods include segmenting a CT image to obtain a cardiac muscle, and estimating the blood flow volume at coronary artery ostia based on a relationship between the size of the organ in an organism and the blood flow volume, found in existing studies. To calculate the blood flow volume of the coronary artery tree based on a non-invasive CT image, the current method needs to segment the CT image to obtain the cardiac muscle and then estimate the blood flow volume according to the size of the cardiac muscle. The steps of this method are relatively complicated.

Therefore, how to provide a simpler and more accurate method and apparatus for acquiring a blood flow volume and a blood flow velocity of a coronary artery has become an urgent technical problem to be solved in the art.

SUMMARY

The technical problem to be solved by the present invention is to provide a simpler method and apparatus for acquiring a blood flow volume and a blood flow velocity of a coronary artery.

In order to solve the above-mentioned problem, the present invention provides a method for acquiring a blood flow volume of a coronary artery, including:
acquiring image information of a coronary artery to obtain geometrical feature data of the coronary artery;
obtaining, according to the geometrical feature data of the coronary artery, the total volume V of a reference lumen of the coronary artery; and calculating a blood flow volume Q at coronary artery ostia according to a formula 1:

$$Q = K * V^{\frac{3}{4}} \qquad \text{Formula 1}$$

wherein when the unit of Q is mm$^3$/s, and when the unit of V is mm$^3$, a value range of K is 5-9.5, preferably 6.5-8, and most preferably 7.

Further, the total volume V of the reference lumen of the coronary artery is obtained by means of the following steps:
the geometrical feature data of the coronary artery including a length of a coronary artery vessel and a reference lumen area of the coronary artery vessel,
cutting the coronary artery vessel along a center line of the vessel into a plurality of sheets perpendicular to the center line of the vessel, defining a bottom area of each sheet as a reference lumen area of the corresponding part, and summing the volumes of the plurality of sheets to obtain the total volume V of the reference lumen of the coronary artery in combination with the length of the coronary artery vessel.

Further, the total volume V of the reference lumen of the coronary artery is obtained by means of the following steps:
recognizing bifurcation kernels of the coronary artery according to the geometrical feature data of the coronary artery; and
the coronary artery including a plurality of bifurcation kernels and a plurality of vascular segments segmented by the bifurcation kernels, summing the volumes of the plurality of bifurcation kernels and the plurality of vascular segments to obtain the total volume V of the reference lumen of the coronary artery.

Further, each bifurcation kernel is simplified into a circular truncated cone to calculate the volume. An area of one bottom surface of the circular truncated cone is a reference lumen area of a proximal end of the bifurcation kernel, and an area of the other bottom surface of the circular truncated cone is a sum of reference lumen areas of two distal ends of the bifurcation kernel; and a height of the circular truncated cone is a distance from the center of the proximal end of the bifurcation kernel to a bifurcation ridge.

Further, the plurality of vascular segments are simplified into circular truncated cones to calculate volumes. Areas of the top and bottom surfaces of each circular truncated cone are respectively a reference lumen area of a proximal end of the corresponding vascular segment and a reference lumen area of a distal end of the corresponding vascular segment; and a height of each circular truncated cone is a length of a center line of the corresponding vascular segment.

Further, the plurality of vascular segments include the most distal vascular segment and other vascular segments other than the most distal vascular segment, wherein: the other vascular segments other than the most distal vascular segment are simplified into cylinders to calculate volumes. A bottom area of each cylinder is a reference lumen area of any part of the vascular segment, and a height of the cylinder is a length of a center line of the vascular segment.

Further, the geometrical feature data includes a bifurcation angle $\alpha_1$ between a proximal main vessel and a distal main vessel of any bifurcation kernel, a full length $L_1$ of the distal main vessel, a bifurcation angle $\alpha_2$ between the proximal main vessel and a branch vessel, a full length $L_2$ of the branch vessel, and any two of a reference lumen area $S_0$ of the proximal main vessel of any bifurcation kernel, a reference lumen area $S_1$ of the proximal end of the distal main vessel of the bifurcation kernel, and a reference lumen area $S_2$ of the proximal end of the branch vessel of the bifurcation kernel; and one remaining reference lumen area is obtained by means of the following formula 2:

$$S_0 = \left(1 - e^{r\frac{\alpha_1 L_1}{\alpha_2 L_2}}\right) S_1 + \left(1 - e^{r\frac{\alpha_2 L_2}{\alpha_1 L_1}}\right) S_2 \quad \text{Formula 2}$$

wherein e is a natural constant, and $-\infty \leq r < -0.6$, preferably $-2 \leq r < 0.75$, and more preferably $r = -1$.

Further, whether a proximal main vessel of a first bifurcation kernel closest to coronary artery vessel ostia has a non-diseased lumen is determined;

if yes, the reference lumen area of the proximal main vessel of the first bifurcation kernel is defined as a reference lumen area of any non-diseased part of the proximal main vessel of the first bifurcation kernel;

all branch vessels on the main vessel where the first bifurcation kernel is located are considered to be not diseased by default, and the reference lumen areas of the proximal ends of all the bifurcated branch vessels on the main vessel where the first bifurcation kernel is located are directly acquired according to the image information; and the reference lumen area of the proximal end of the distal main vessel connected to any bifurcation kernel is calculated one by one from near to far by means of the reference lumen area of the proximal main vessel of any bifurcation kernel and the reference lumen area of the proximal end of the branch vessel according to a distance between any bifurcation kernel on the main vessel where the first bifurcation kernel is located and the coronary artery vessel ostia.

Further, if the proximal main vessel of the first bifurcation kernel closest to the coronary artery vessel ostia does not have a non-diseased lumen, whether the proximal end of the most distal vessel is diseased is determined;

if no, the reference lumen area of the proximal end of the most distal vessel is directly acquired according to the image information; and the reference lumen area of the proximal main vessel connected to any bifurcation kernel is calculated one by one from far to near by means of the reference lumen of the proximal end of the distal main vessel and the proximal end of the branch vessel of any bifurcation kernel according to a distance between the bifurcation kernel and the coronary artery vessel ostia.

Further, a reference lumen area of a region of interest in the coronary artery vessel is obtained by the following method:

the geometrical characteristic data of the coronary artery includes a tunica media inner-circumference area $S'$ of the region of interest in the coronary artery vessel, and the reference lumen area $S = A*S'$ of a corresponding region, wherein $0.7 \leq A < 1$.

Further, the image information of the coronary artery is acquired by means of non-invasive coronary artery CT radiography.

Further, the present invention further provides a method for acquiring a blood flow velocity of a coronary artery. The blood flow velocity at coronary artery ostia is obtained by dividing the blood flow volume at the coronary artery ostia, obtained according to any one of the previously described methods, by the reference lumen area at the ostia.

Further, after the blood flow velocity at t the coronary artery ostia is obtained, the blood flow velocity of any vascular segment in the coronary artery other than the coronary artery ostia is calculated stage by stage by means of the following formula 3 or formula 4:

$$v_1 = v_0 \left(1 - e^{r\frac{\alpha_1 L_1}{\alpha_2 L_2}}\right) \quad \text{Formula 3}$$

$v_0$ is a blood flow velocity of a proximal main vessel of each bifurcation kernel, and $v_1$ is a blood flow velocity of a distal main vessel of the bifurcation kernel;

$$v_2 = v_0 \left(1 - e^{r\frac{\alpha_1 L_1}{\alpha_2 L_2}}\right) \quad \text{Formula 4}$$

$v_2$ is a blood flow velocity of a branch vessel of each bifurcation kernel.

Further, the present invention further provides an apparatus for acquiring a blood flow volume of a coronary artery, including:

a coronary artery geometrical feature analysis module, configured to acquire image information of a coronary artery to obtain geometrical feature data of the coronary artery;

a volume calculation module, configured to obtain the total volume V of a reference lumen of the coronary artery according to the geometrical feature data of the coronary artery; and a blood flow volume calculation module, configured to calculate a blood flow volume Q at coronary artery ostia according to a formula 1:

$$Q = K * V^{\frac{3}{4}} \quad \text{Formula 1}$$

wherein when the unit of Q is mm$^3$/s, and when the unit of V is mm$^3$, a value range of K is 5–9.5, preferably 6.5–8, and most preferably 7.

Further, the coronary artery geometrical feature analysis module is configured to acquire a length of a coronary artery vessel and a reference lumen area of the coronary artery vessel;

the volume calculation module is configured to cut the coronary artery vessel along a center line of the vessel into a plurality of sheets perpendicular to the center line of the vessel, define a bottom area of each sheet as a reference lumen area of the corresponding part, and sum the volumes of the plurality of sheets to obtain the total volume V of the reference lumen of the coronary artery in combination with the length of the coronary artery vessel.

Further, the volume calculation module is configured to recognize bifurcation kernels of the coronary artery according to the geometrical feature data of the coronary artery; and the coronary artery including a plurality of bifurcation kernels and a plurality of vascular segments segmented by the bifurcation kernels, sum the volumes of the plurality of bifurcation kernels and the plurality of vascular segments to obtain the total volume V of the reference lumen of the coronary artery.

Further, the volume calculation module is configured to simplify each bifurcation kernel into a circular truncated cone to calculate the volume; an area of one bottom surface of the circular truncated cone is a reference lumen area of a proximal end of the bifurcation kernel, and an area of the other bottom surface of the circular truncated cone is a sum of reference lumen areas of two distal ends of the bifurcation kernel; and a height of the circular truncated cone is a distance from the center of the proximal end of the bifurcation kernel to a bifurcation ridge.

Further, the volume calculation module is configured to simplify the plurality of vascular segments into circular truncated cones to calculate volumes; areas of the top and bottom surfaces of each circular truncated cone are respectively a reference lumen area of a proximal end of the corresponding vascular segment and a reference lumen area of a distal end of the corresponding vascular segment; and a height of each circular truncated cone is a length of a center line of the corresponding vascular segment.

Further, the plurality of vascular segments include the most distal vascular segment and other vascular segments other than the most distal vascular segment, wherein: the volume calculation module is configured to simplify the other vascular segments other than the most distal vascular segment into cylinders to calculate volumes. A bottom area of each cylinder is a reference lumen area of any part of the vascular segment, and a height of the cylinder is a length of a center line of the vascular segment.

Further, the coronary artery geometrical feature analysis module is configured to acquire a bifurcation angle $\alpha_1$ between a proximal main vessel and a distal main vessel of any bifurcation kernel, a full length $L_1$ of the distal main vessel, a bifurcation angle $\alpha_2$ between the proximal main vessel and a branch vessel, a full length $L_2$ of the branch vessel, and any two of a reference lumen area $S_0$ of the proximal main vessel of any bifurcation kernel, a reference lumen area $S_1$ of the proximal end of the distal main vessel of the bifurcation kernel, and a reference lumen area $S_2$ of the proximal end of the branch vessel of the bifurcation kernel; and obtain one remaining reference lumen area by means of the following formula 2:

$$S_0 = \left(1 - e^{r\frac{\alpha_1 L_1}{\alpha_2 L_2}}\right) S_1 + \left(1 - e^{e^{r\frac{\alpha_2 L_2}{\alpha_1 L_1}}}\right) S_2 \quad \text{Formula 2}$$

wherein e is a natural constant, and $-\infty \leq r < -0.6$, preferably $-2 \leq r < 0.75$, and most preferably $r = -1$.

Further, the coronary artery geometrical feature analysis module is configured to determine whether a proximal main vessel of a first bifurcation kernel closest to coronary artery vessel ostia has a non-diseased lumen;

if yes, define the reference lumen area of the proximal main vessel of the first bifurcation kernel as a reference lumen area of any non-diseased part of the proximal main vessel of the first bifurcation kernel;

consider all branch vessels on the main vessel where the first bifurcation kernel is located to be not diseased by default, and directly acquire, according to the image information, the reference lumen areas of the proximal ends of all the bifurcated branch vessels on the main vessel where the first bifurcation kernel is located;

calculate the reference lumen area of the proximal end of the distal main vessel connected to any bifurcation kernel one by one from near to far by means of the reference lumen area of the proximal main vessel of any bifurcation kernel and the reference lumen area of the proximal end of the branch vessel according to a distance between any bifurcation kernel on the main vessel where the first bifurcation kernel is located and the coronary artery vessel ostia; and if the proximal main vessel of the first bifurcation kernel closest to the coronary artery vessel ostia does not have a non-diseased lumen, determine whether the proximal end of the most distal vessel is diseased;

if no, directly acquire the reference lumen area of the proximal end of the most distal vessel according to the image information; and calculate the reference lumen area of the proximal main vessel connected to any bifurcation kernel one by one from far to near by means of the reference lumen of the proximal end of the distal main vessel and the proximal end of the branch vessel of any bifurcation kernel according to a distance between the bifurcation kernel and the coronary artery vessel ostia.

Further, the coronary artery geometrical feature analysis module is configured to acquire a reference lumen area of a region of interest in the coronary artery vessel, including:

acquiring a tunica media inner-circumference area S' of the region of interest in the coronary artery vessel, and the reference lumen area $S = A*S'$ of a corresponding region, wherein $0.7 \leq A < 1$.

Further, the coronary artery geometrical feature analysis module acquires the image information of the coronary artery by means of non-invasive coronary artery CT radiography.

Further, the present invention provides an apparatus for acquiring a blood flow velocity of a coronary artery, including:

any one of the previously described apparatuses for acquiring the blood flow volume of the coronary artery, configured to acquire a blood flow volume at coronary artery ostia; and a blood flow velocity calculation module, configured to obtain a blood flow velocity at the coronary artery ostia by dividing the blood flow volume at the coronary artery ostia by the reference lumen area at the ostia.

Further, the blood flow velocity calculation module is configured to calculate the blood flow velocity of any vascular segment in the coronary artery other than the coronary artery ostia stage by stage by means of the following formula 3 or formula 4 after the blood flow velocity at the coronary artery ostia is obtained:

$$v_1 = v_0 \left(1 - e^{r\frac{\alpha_1 L_1}{\alpha_2 L_2}}\right) \quad \text{Formula 3}$$

$v_0$ is a blood flow velocity of a proximal main vessel of each bifurcation kernel, and $v_1$ is a blood flow velocity of a distal main vessel of the bifurcation kernel;

$$v_2 = v_0 \left(1 - e^{r\frac{\alpha_1 L_1}{\alpha_2 L_2}}\right) \quad \text{Formula 4}$$

$v_2$ is a blood flow velocity of a branch vessel of each bifurcation kernel.

Further, the present invention further provides another apparatus for acquiring a blood flow volume of a coronary artery, including:

a processor, a memory, and a computer-executable instruction stored in the memory. The processor, when executing the computer-executable instruction, implements any one of the previously described methods for acquiring the blood flow volume of the coronary artery.

Further, the present invention provides an apparatus for acquiring a blood flow velocity of a coronary artery, including:

a processor, a memory, and a computer-executable instruction stored in the memory. The processor, when executing the computer-executable instruction, implements any one of the previously described methods for acquiring the blood flow velocity of the coronary artery.

In conclusion, the present invention provides the novel methods for acquiring the blood flow volume and the blood flow velocity of the coronary artery. The blood flow volume and the blood flow velocity of the coronary artery can be obtained by means of the image information of the coronary artery. Compared with the method, in the prior art, for estimating the blood flow volume of the coronary artery by means of the size of a cardiac muscle of a patient, the method is simpler. Compared with hemodynamic calculation without using a personalized blood flow of the patient, the method can improve the accuracy of a hemodynamic result and can provide a more accurate boundary condition for image-based hemodynamic calculation. Furthermore, the image information in the present invention can be directly obtained invasively, without injuring the human body.

BRIEF DESCRIPTION OF THE DRAWINGS

The present invention is further described in detail below in combination with accompanying drawings and specific implementation modes.

DETAILED DESCRIPTION

Preferred implementation modes of the present invention are described in detail now in combination with accompanying drawings. Although the description of the present invention will be introduced in conjunction with the implementation modes, this does not mean that the features of the present invention are limited to the several implementation modes. On the contrary, the purpose of introducing the invention in combination with the implementation modes is to cover other options or modifications that may be extended based on the claims of the present invention. In order to provide a deep understanding of the present invention, the following description will contain many specific details. The present invention can also be implemented without using these details. In addition, in order to avoid confusing or obscuring the focus of the present invention, some specific details will be omitted in the description.

Figure 1:
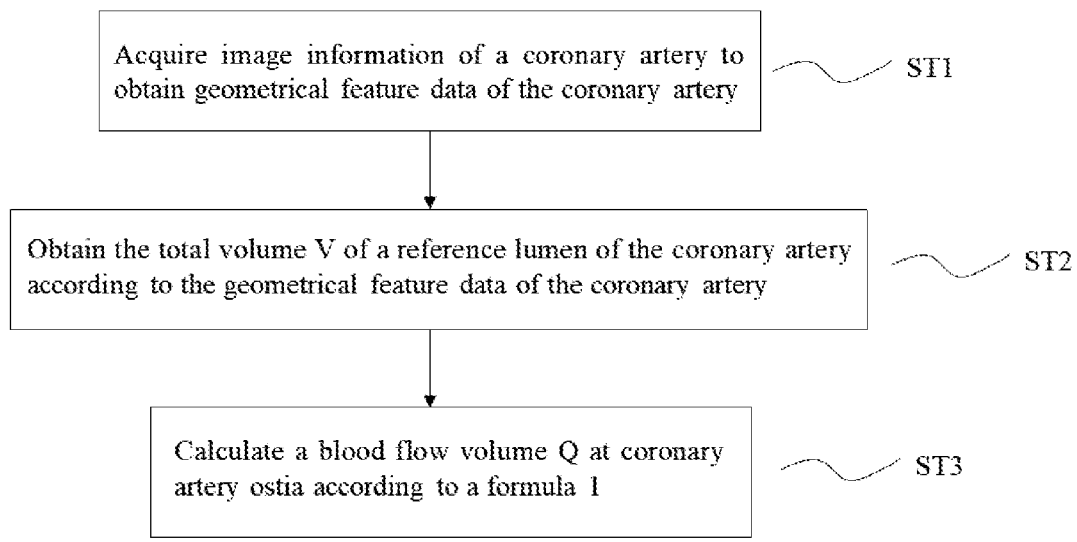
FIG. 1 is a flow schematic diagram of a method for acquiring a blood flow volume of a coronary artery in the present invention.

The inventor of the present invention found a relationship between a volume of a coronary artery and a blood flow volume at coronary artery ostia based on the "allometric growth law". Based on this, a large number of coronary artery samples are selected; a specific relationship between a blood flow volume at the coronary artery ostia and a total volume of the coronary artery is determined according to experimental data of the large number of samples; and a method for acquiring a blood flow volume of a coronary artery is finally provided. As shown in FIG. 1, the method includes:

ST1: image information of the coronary artery is acquired to obtain geometrical feature data of the coronary artery. The geometrical feature data of the coronary artery can include original geometrical feature data of the coronary artery directly obtained through the image information of the coronary artery, and can also include geometrical feature data of a reference lumen of the coronary artery obtained by reconstructing a disease-free state of the coronary artery by means of the original geometrical feature data of the coronary artery.

ST2: a total volume V of the reference lumen of the coronary artery is obtained according to the geometrical feature data of the coronary artery.

ST3: a blood flow volume Q at coronary artery ostia is calculated according to a formula 1:

$$Q = K * V^{\frac{3}{4}} \quad \text{Formula 1}$$

wherein when the unit of Q is mm$^3$/s, and when the unit of V is mm$^3$, K is a coefficient determined through experiments on the large number of samples, and a value range of K is 5-9.5, preferably 6.5-8, and most preferably 7.

It should be noted that if the blood flow volume Q at the coronary artery ostia and the unit of the total volume V of the reference lumen of the coronary artery change, the value range of K also correspondingly changes in an order of magnitude.

In the prior art, some people use a method for estimating a blood flow volume by a volume of an actual lumen of a coronary artery. Compared with the volume of the actual lumen, the reference lumen used in the present invention can better reflect the blood flow volume in a congestion state. Since the blood flow volume required by myocardium perfusion may not decrease due to coronary artery stenosis, using the volume of the actual lumen may cause underestimation of the blood flow volume.

In the present invention, the volume of the reference lumen of the coronary artery is used to calculate the flow velocity, so that more accurate boundary conditions can be provided for hemodynamic calculation.

It should be noted that a proximal end in the present invention refers to one end closer to the coronary artery ostia, and a distal end corresponds to one end farther from the coronary artery ostia.

A proximal main vessel, a distal main vessel and a branch vessel are relative concepts. For any bifurcation, a main vessel at one end closer to the coronary artery ostia is the proximal main vessel, a main vessel at one end farther from the coronary artery ostia is the distal main vessel, and the other one is the branch vessel. When the current branch vessel is subjected to two-stage bifurcation to obtain two stages of branches, for the two-stage bifurcation, the branch vessel is a main vessel, and the two stages of branches are branch vessels.

The total volume V of the reference lumen of the coronary artery in the present invention can be obtained by any known method in the prior art.

In one embodiment of the present invention, the volume V of the reference lumen of the coronary artery can be obtained by the following steps:

ST1': image information of the coronary artery is acquired to obtain geometrical feature data of the coronary artery including a length of a coronary artery vessel and a reference lumen area of the coronary artery vessel;

ST2': the coronary artery vessel is cut along a center line of the vessel into a plurality of sheets perpendicular to the center line of the vessel, a bottom area of each sheet is defined as a reference lumen area of the corresponding part, and the volumes of the plurality of sheets are summed to obtain the total volume V of the reference lumen of the coronary artery in combination with the length of the coronary artery vessel. That is, the reference lumen of the coronary artery is simplified into a superposition of N extremely thin sheets, so that the total volume V of the reference lumen of the coronary artery can be obtained by means of a summation formula for a cross-sectional area of the coronary artery and the length of the vessel, as mentioned below:

$$V = \sum_{i=1}^{N}(S_i \Delta h_i)$$

wherein $S_i$ and $\Delta h_i$ represent an area and a thickness of an ith thin sheet of the reference lumen of the coronary artery, and N is a total number of the simplified thin sheets. It can be understood that if N is larger, the obtained volume V of the reference lumen of the coronary artery is more accurate. During calculation, a proper value of N can be selected according to a need of the situation.

In another embodiment of the present invention, for convenience of calculation, the volume V of the reference lumen of the coronary artery can be obtained by the following steps:

ST1'': image information of the coronary artery is acquired to obtain geometrical feature data of the coronary artery including a length of the coronary artery and a reference lumen area; and ST21'': bifurcation kernels of the coronary artery are recognized according to the geometrical feature data of the coronary artery.

Wherein, the bifurcation kernels can be determined by any method for recognizing bifurcation kernels in the art, as long as a calculation error is within an acceptable range.

Figure 2:
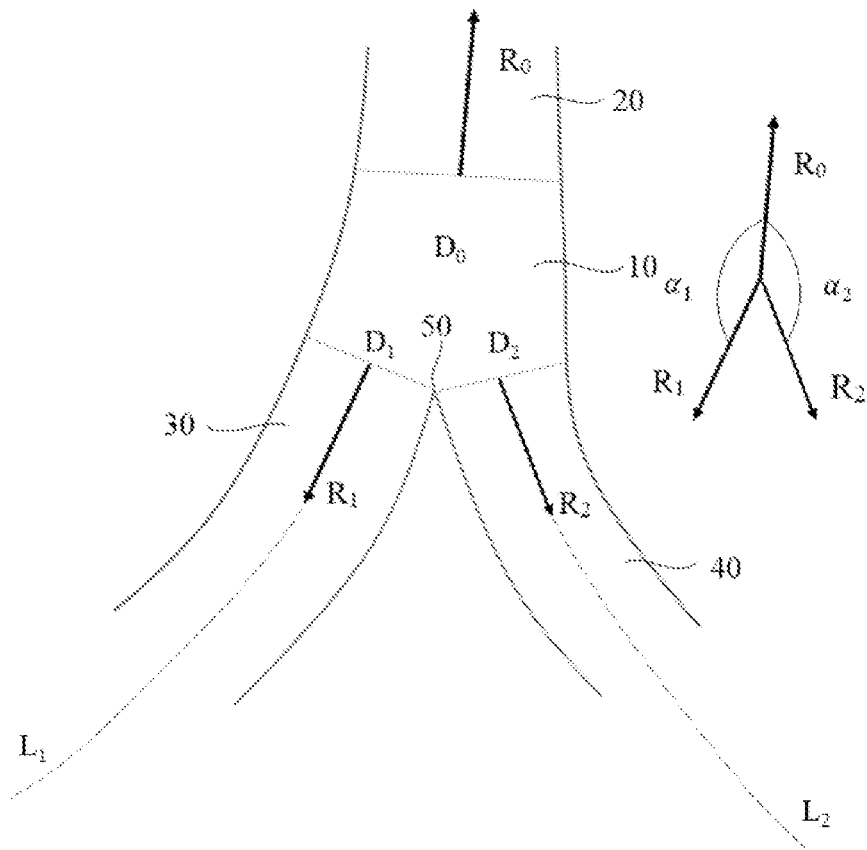
FIG. 2 is a schematic structural diagram of a bifurcation kernel in the present invention.

In one preferred embodiment of the present invention, as shown in FIG. 2, the bifurcation kernel is a region encircled by a first cross section $D_0$ of a begin-to-grow part of a proximal main vessel 20 of this bifurcation, a second cross section $D_1$ of a distal main vessel 30 at a bifurcation ridge 50, a third cross section $D_2$ of a branch vessel 40 at the bifurcation ridge 50, and a vascular wall, wherein boundary points between the main vessels and the distal end of the branch vessel are bifurcation ridges.

ST22': the coronary artery can be segmented into a plurality of vascular segments by means of bifurcation kernels, i.e., the coronary artery includes a plurality of bifurcation kernels and a plurality of vascular segments segmented by the bifurcation kernels, and the volumes of the plurality of bifurcation kernels and the plurality of vascular segments are summed to obtain the total volume V of the reference lumen of the coronary artery.

Wherein, each bifurcation kernel is simplified into a circular truncated cone to calculate its volume. An area of one bottom surface of the circular truncated cone is a reference lumen area of a proximal end of the bifurcation kernel, i.e., an area of the first cross section Do, and an area of the other bottom surface of the circular truncated cone is a sum of reference lumen areas of two distal ends of the bifurcation kernel, i.e., an area sum of the second cross section $D_1$ and the third cross section $D_2$. The height of the circular truncated cone is a distance from the center of the proximal end of the bifurcation kernel to the bifurcation ridge. The center of the proximal end of the bifurcation kernel here refers to the center of the first cross section Do.

The plurality of vascular segments are simplified into circular truncated cones to calculate their volumes. Areas of the top and bottom surfaces of each circular truncated cone are respectively a reference lumen area of a proximal end of the corresponding vascular segment and a reference lumen area of a distal end of the corresponding vascular segment. The height of each circular truncated cone is a length of a center line of the corresponding vascular segment.

Further, the plurality of vascular segments are divided into the most distal vascular segment and other vascular segments other than the most distal vascular segment according to the structural characteristics of the coronary artery vessel. In the coronary artery vessel, the reference lumen area of the most distal vascular segment may gradually decrease in a lengthwise direction of the vessel. For any other vascular segments other than the most distal vascular segment, in the same vascular segment, the reference lumen area is the same.

Therefore, the other vascular segments other than the most distal vascular segment are simplified into cylinders to calculate their volumes. A bottom area of each cylinder is a reference lumen area of any part of the vascular segment, and the height of the cylinder is a length of a center line of the vascular segment. The most distal vascular segment is simplified into a circular truncated cone. Areas of the top and bottom surfaces of the circular truncated cone are respectively the reference lumen area of the proximal end of the most distal vascular segment and the reference lumen area of the distal end. The height of the circular truncated cone is the length of the center line of the vascular segment.

Further, in the ST1, the original geometric feature data of the coronary artery can be directly obtained according to the image information of coronary artery, including the length of the coronary artery vessel, a bifurcation angle, and an original lumen area. For a diseased lumen, the lumen area needs to be corrected to obtain a lumen area in a normal state and a reference lumen area. For a non-diseased lumen, the actual lumen area is the reference lumen area.

In an existing method for coronary artery estimation, the reference lumen area is mostly calculated by selecting normal lumen positions before and after a disease, and taking a mean value of areas of the normal lumens as the size of the reference lumen at a diseased position. However, in the case that the coronary artery has a diffuse disease, the coronary artery contains a relatively long disease distribution region, and it is relatively hard to find a normal lumen near the diseased vascular segment, so that the traditional method is not applicable to a patient suffering from the diffuse disease in the whole vessel since the size of the reference lumen is easy to underestimate.

The inventor of the present application found in a study that in a bifurcation structure of the coronary artery as shown in FIG. 2, the blood flow velocity of the proximal main vessel, the blood flow velocity of the proximal end of the distal main vessel, and the blood flow velocity of the proximal end of the branch vessel of any bifurcation kernel have the following relationship:

$$v_1 = v_0\left(1 - e^{r\frac{\alpha_1 L_1}{\alpha_2 L_2}}\right)  \quad \text{Formula 3}$$

$v_0$ is a blood flow velocity of a proximal main vessel of each bifurcation kernel, and $v_1$ is a blood flow velocity of a distal main vessel of the bifurcation kernel;

$$v_2 = v_0\left(1 - e^{r\frac{\alpha_2 L_2}{\alpha_1 L_1}}\right) \quad \text{Formula 4}$$

$v_2$ is a blood flow velocity of a branch vessel of each bifurcation kernel,
wherein e is a natural constant, and r is a coefficient of a power of e determined after experiments on a large number of samples, $-\infty \le r < -0.6$, preferably $-2 \le r < 0.75$ in order to make a calculation result more accurate, and more preferably $r=-1$;
$\alpha_1$ is a bifurcation angle between the proximal main vessel and the distal main vessel; $L_1$ is a full length of the distal main vessel; $\alpha_2$ is a bifurcation angle between the proximal main vessel and the branch vessel; and $L_2$ is a full length of the branch vessel.

It should be understood that in general definitions in the art, as shown in FIG. 2, the bifurcation angle $\alpha_1$ is an included angle between a normal $R_0$ of the cross section $D_0$ of the proximal main vessel at the begin-to-grow part of the vessel and a normal $R_1$ of the cross section $D_1$ of the distal main vessel at the bifurcation ridge; the bifurcation angle $\alpha_2$ is an included angle between $R_0$ and a normal $R_2$ of the cross section $D_2$ of the branch vessel at the bifurcation ridge; the full length $L_1$ of the distal main vessel is a full length from the bifurcation center to the distal end of the most distal vascular segment of the distal main vessel (not the length of this vascular segment of the distal main vessel); and the full length $L_2$ of the branch vessel is a full length from the bifurcation center to the distal end of the most distal vascular segment of the branch vessel (not the length of this vascular segment of the branch vessel). The bifurcation center is generally the gravity center of the bifurcation kernel. However, in the present invention, an error caused by calculating the length of the vessel by selecting any point in the bifurcation kernel as the bifurcation center can be acceptable.

Further, for any bifurcation kernel, the reference lumen area $S_0$ of the proximal end of the bifurcation kernel, the reference lumen area $S_1$ of the position of the bifurcation kernel adjacent to the distal main vessel, and the reference lumen area $S_2$ of the position of the bifurcation kernel adjacent to the branch vessel have the following relationship: $v_0*S_0=v_1*S_1+v_2*S_2$ based on the flow conservation principle, so that it can be obtained that a relationship of the following formula 2 on any bifurcation kernel:

$$S_0 = \left(1 - e^{r\frac{\alpha_1 L_1}{\alpha_2 L_2}}\right)S_1 + \left(1 - e^{r\frac{\alpha_1 L_1}{\alpha_2 L_2}}\right)S_2 \quad \text{Formula 2}$$

wherein $S_0$ is the reference lumen area of the proximal end of the bifurcation kernel. Meanwhile, the proximal main vessel of one bifurcation kernel is not possibly the most distal vascular segment, so that the reference lumen area of any position on the proximal main vessel shall be the same, i.e., $S_0$ is also the reference lumen area of the proximal main vessel of the bifurcation kernel;
$S_1$ is the reference lumen area of the part of the bifurcation kernel adjacent to the distal main vessel, and is also the reference lumen area of the proximal end of the distal main vessel of the bifurcation kernel. When the distal main vessel is other vascular segments other than the most distal vascular segment, the reference lumen area of any part on the distal main vessel is equal to the reference lumen area of the proximal end of the distal main vessel;
$S_2$ is the reference lumen area of the part of the bifurcation kernel adjacent to the branch vessel, and is also the reference lumen area of the proximal end of the branch vessel of the bifurcation kernel. When the branch vessel is other vascular segments other than the most distal vascular segment, the reference lumen area of any part on the branch vessel is equal to the reference lumen area of the proximal end of the branch vessel.

On the basis of this, the present invention provides a method capable of calculating a reference lumen according to an anatomical structure of a coronary bifurcation, so that a more accurate reference lumen calculation method can be provided for a patient suffering from a diffuse disease in the coronary artery, and then more accurate boundary conditions can be provided for hemodynamic calculation.

The geometrical feature data of the coronary artery is obtained by means of the image information of the coronary artery, and the geometrical feature data includes the bifurcation angle $\alpha_1$ between the proximal main vessel and the distal main vessel of any bifurcation kernel, the full length $L_1$ of the distal main vessel, the bifurcation angle $\alpha_2$ between the proximal main vessel and the branch vessel, and the full length $L_2$ of the branch vessel; and any two of the reference lumen area $S_0$ of the proximal main vessel of any bifurcation kernel, the reference lumen area $S_1$ of the proximal end of the distal main vessel of the bifurcation kernel, and the reference lumen area $S_2$ of the proximal end of the branch vessel of the bifurcation kernel; and then one remaining reference lumen area is obtained by means of the formula 2.

In an actual process of calculating the blood flow volume, reference lumens of diseased vessels can be calculated one by one according to an actual disease condition of the coronary artery.

Figure 3:
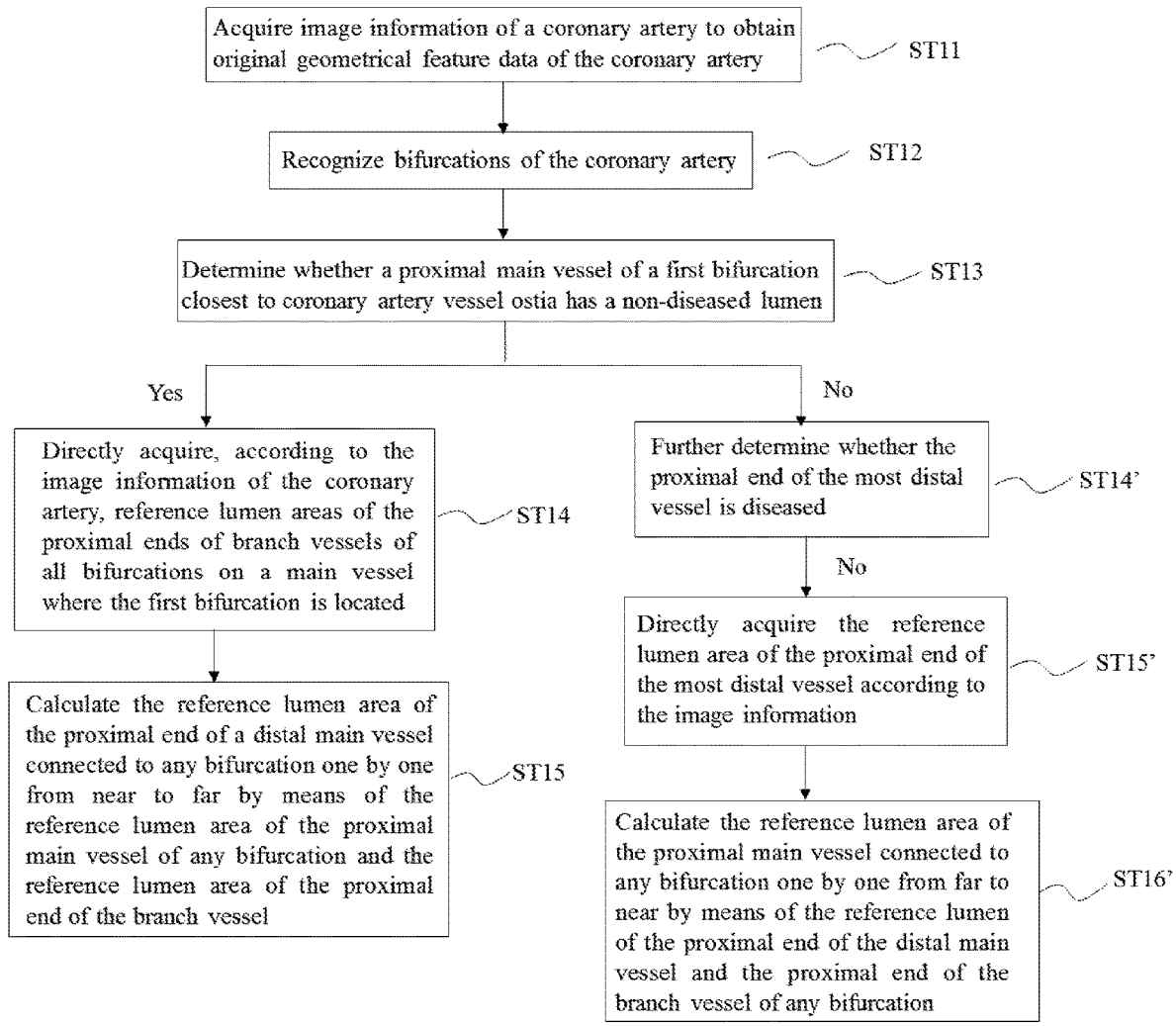
FIG. 3 is a flow schematic diagram of a method for acquiring a reference lumen area of an entire coronary artery in the embodiments of the present invention.

Further, in order to facilitate automatic calculation for the reference lumen of the whole coronary artery vessel, as shown in FIG. 3, the present invention further provides methods for calculating the reference lumen areas of the coronary artery one by one from far to near and from near to far.

Figure 4:
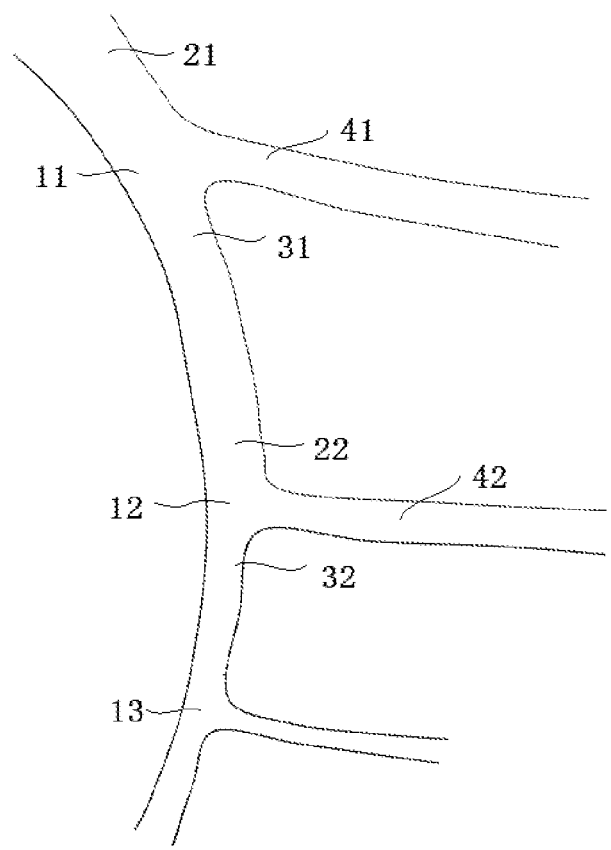
FIG. 4 is a schematic diagram of a simplified structure of part of the coronary artery vessel in the present invention.

In one embodiment of the present invention, in combination with FIG. 4, the method for calculating the reference lumen areas of the whole coronary artery vessel from near to far includes the following specific steps:
ST11: image information of the coronary artery is acquired to obtain original geometrical feature data of the coronary artery;
ST12: bifurcation kernels of the coronary artery are recognized;
ST13: whether the proximal main vessel of the first bifurcation kernel closest to the coronary artery vessel ostia has a non-diseased lumen is determined: it is considered that there is a non-diseased lumen as long as any part on the proximal main vessel of the first bifurcation kernel has a normal lumen area;

ST14: if yes, the reference lumen area of the proximal main vessel of the first bifurcation kernel is defined as the reference lumen area of any non-diseased part of the proximal main vessel of the first bifurcation kernel;

all branch vessels on the main vessel where the first bifurcation kernel is located are considered to be not diseased by default, and the reference lumen areas of the proximal ends of the branch vessels of all the bifurcation kernels on the main vessel where the first bifurcation kernel is located are directly acquired according to the image information of the coronary artery; and ST15: the reference lumen area of the proximal end of the distal main vessel connected to any bifurcation kernel is calculated one by one from near to far by means of the reference lumen area of the proximal main vessel of any bifurcation kernel and the reference lumen area of the proximal end of the branch vessel according to a distance between any bifurcation kernel on the main vessel where the first bifurcation kernel is located and the coronary artery vessel ostia.

Specifically, in combination with FIG. 4, the method for calculating the whole coronary artery from near to far is as follows:

ST141: the reference lumen area of the proximal end of the distal main vessel 31 of the first bifurcation kernel 11 is calculated by means of the reference lumen area of the proximal main vessel 21 of the first bifurcation kernel 11 and the reference lumen area of the proximal end of the first branch vessel 41;

further, the distal main vessel 31 of the first bifurcation kernel 11 is the proximal main vessel 22 of the second bifurcation kernel 12, and the reference lumen area of the proximal end of the distal main vessel 31 of the first bifurcation kernel 11 is the reference lumen area of the proximal main vessel 22 of the second bifurcation kernel 12;

ST142: the reference lumen area of the proximal end of the distal main vessel 32 of the second bifurcation kernel 12 is calculated by means of the reference lumen area of the proximal main vessel 22 of the second bifurcation kernel 12 and the reference lumen area of the proximal end of the second branch vessel 42;

ST143: the rest can be done in the same manner, i.e., the reference lumen areas of the distal main vessels from the third bifurcation kernel 13 to the most distal bifurcation kernel are calculated one by one from near to far to finally obtain the reference lumen areas of all the vascular segments on this main vessel.

In another embodiment of the present invention, a method from far to near can also be used to calculate the reference lumen areas of all the vascular segments stage by stage. For example:

ST11: image information of the coronary artery is acquired to obtain original geometrical feature data of the coronary artery;

ST12: bifurcation kernels of the coronary artery are recognized;

ST13: whether the proximal main vessel of the first bifurcation kernel closest to the coronary artery vessel ostia has a non-diseased lumen is determined;

ST14': if the proximal main vessel of the first bifurcation kernel closest to the coronary artery vessel ostia does not have a non-diseased lumen, whether the proximal end of the most distal vessel is diseased is further determined;

ST15': if no, the reference lumen area of the proximal end of the most distal vessel is directly acquired according to the image information; and ST16': the reference lumen area of the proximal main vessel connected to any bifurcation kernel is calculated one by one from far to near by means of the reference lumen areas of the proximal end of the distal main vessel and the proximal end of the branch vessel of any bifurcation kernel according to a distance between the bifurcation kernel and the coronary artery vessel ostia.

In addition to the previously described method for calculating the reference lumens of the whole coronary artery by means of the relationship among the reference lumen areas of the proximal main vessel, the distal main vessel and the branch vessel on the same bifurcation kernel, the present invention further provides another method for calculating the reference lumens of the coronary artery. A vascular wall generally includes the intima, the tunica media and the adventitia in sequence from the lumen surface to the outside: the intima is the innermost layer of the vascular wall which is a region where disease plaques grow, with an intima inner-circumference area serving as an actual lumen area, and the tunica media is located between the intima and the adventitia and is in tight fit with the outer side of the intima, with a tunica media inner-circumference area serving as an intima outer-circumference area, so that the reference lumen area of a region of interest in the coronary artery vessel can also be calculated by the following method:

geometrical feature parameters of the coronary artery are acquired according to the image information of the coronary artery, and the geometrical feature data of the coronary artery includes the tunica media inner-circumference area S' of the region of interest in the coronary artery vessel, and the reference lumen area S=A*S' of a corresponding region, wherein 0.7≤A<1.

Further, the image information of the coronary artery can be acquired by means of non-invasive coronary artery CT radiography in the present invention, so that the blood flow information of the coronary artery can be obtained without an additional trauma, and the pain of the patient is greatly relieved.

Further, the present invention further provides a method for acquiring a blood flow velocity of a coronary artery. The blood flow velocity at the coronary artery ostia is obtained by dividing the blood flow volume at the coronary artery ostia, obtained according to any one of the previously described methods, by the reference lumen area at the ostia.

Further, after the blood flow velocity at the coronary artery ostia is obtained, the blood flow velocity of any vascular segment in the coronary artery other than the coronary artery ostia is calculated stage by stage by means of the following formula 3 or formula 4:

$$v_1 = v_0\left(1 - e^{r\frac{\alpha_1 L_1}{\alpha_2 L_2}}\right) \quad \text{Formula 3}$$

$v_0$ is the blood flow velocity of the proximal main vessel of the bifurcation, and $v_1$ is the blood flow velocity of the distal main vessel of the bifurcation;

$$v_2 = v_0\left(1 - e^{r\frac{\alpha_2 L_2}{\alpha_1 L_1}}\right) \quad \text{Formula 4}$$

$v_2$ is the blood flow velocity of the branch vessel of the bifurcation, where $\alpha_1$, $\alpha_2$, $L_1$, $L_2$ and r have the same definitions as before.

Existing methods for calculating a blood flow velocity of a bifurcation are mostly to calculate a blood flow velocity ratio based on the size of a lumen of an opening of the bifurcation. Information of bifurcation angles and bifurcation lengths is added into a bifurcation model proposed by the method, so that the accuracy for calculating the blood flow velocity ratio of the bifurcation is further improved.

Further, the present invention further provides an apparatus for acquiring a blood flow volume of a coronary artery, including:

a coronary artery geometrical feature analysis module, configured to acquire image information of the coronary artery to obtain geometrical feature data of the coronary artery;

a volume calculation module, configured to obtain the total volume V of a reference lumen of the coronary artery according to the geometrical feature data of the coronary artery; and a blood flow volume calculation module, configured to calculate a blood flow volume Q at coronary artery ostia according to a formula 1:

$$Q = K * V^{\frac{3}{4}} \qquad \text{Formula 1}$$

wherein when the unit of Q is mm³/s, and when the unit of V is mm³, a value range of K is 5-9.5, preferably 6.5-8, and most preferably 7.

Further, the coronary artery geometrical feature analysis module is configured to acquire a length of the coronary artery vessel and a reference lumen area of the coronary artery vessel;

the volume calculation module is configured to cut the coronary artery vessel along the center line of the vessel into a plurality of sheets perpendicular to the center line of the vessel, define a bottom area of each sheet as the reference lumen area of the corresponding part, and sum the volumes of the plurality of sheets to obtain the total volume V of the reference lumen of the coronary artery in combination with the length of the coronary artery vessel.

Further, the volume calculation module is configured to recognize bifurcation kernels of the coronary artery according to the geometrical feature data of the coronary artery.

The coronary artery includes a plurality of bifurcation kernels and a plurality of vascular segments segmented by the bifurcation kernels, and the volumes of the plurality of bifurcation kernels and the plurality of vascular segments are summed to obtain the total volume V of the reference lumen of the coronary artery.

Further, the volume calculation module is configured to simplify each bifurcation kernel into a circular truncated cone to calculate the volume. An area of one bottom surface of the circular truncated cone is a reference lumen area of a proximal end of the bifurcation kernel, and an area of the other bottom surface of the circular truncated cone is a sum of reference lumen areas of two distal ends of the bifurcation kernel. The height of the circular truncated cone is a distance from the center of the proximal end of the bifurcation kernel to a bifurcation ridge.

Further, the volume calculation module is configured to simplify the plurality of vascular segments into circular truncated cones to calculate volumes. Areas of the top and bottom surfaces of each circular truncated cone are respectively a reference lumen area of a proximal end of the corresponding vascular segment and a reference lumen area of a distal end of the corresponding vascular segment. The height of each circular truncated cone is a length of the center line of the corresponding vascular segment.

Further, the plurality of vascular segments include the most distal vascular segment and other vascular segments other than the most distal vascular segment, wherein:

The volume calculation module is configured to simplify the other vascular segments other than the most distal vascular segment into cylinders to calculate volumes. A bottom area of each cylinder is a reference lumen area of any part of the vascular segment, and the height of the cylinder is a length of the center line of the vascular segment.

Further, the coronary artery geometrical feature analysis module is configured to acquire a bifurcation angle $\alpha_1$ between a proximal main vessel and a distal main vessel of any bifurcation kernel, a full length $L_1$ of the distal main vessel, a bifurcation angle $\alpha_2$ between the proximal main vessel and a branch vessel, a full length $L_2$ of the branch vessel, and any two of a reference lumen area $S_0$ of the proximal main vessel of any bifurcation kernel, a reference lumen area $S_1$ of the proximal end of the distal main vessel of the bifurcation kernel, and a reference lumen area $S_2$ of the proximal end of the branch vessel of the bifurcation kernel; and obtain one remaining reference lumen area by means of the following formula 2:

$$S_0 = \left(1 - e^{r\frac{\alpha_1 L_1}{\alpha_2 L_2}}\right) S_1 + \left(1 - e^{r\frac{\alpha_2 L_2}{\alpha_1 L_1}}\right) S_2 \qquad \text{Formula 2}$$

wherein e is a natural constant; and $-\infty \leq r < -0.6$, preferably $-2 \leq r < 0.75$, and most preferably $r = -1$.

Further, the coronary artery geometrical feature analysis module is configured to determine whether the proximal main vessel of the first bifurcation kernel closest to the coronary artery vessel ostia has a non-diseased lumen;

if yes, define the reference lumen area of the proximal main vessel of the first bifurcation kernel as the reference lumen area of any non-diseased part of the proximal main vessel of the first bifurcation kernel;

consider all branch vessels on the main vessel where the first bifurcation kernel is located to be not diseased by default, and directly acquire, according to the image information, the reference lumen areas of the proximal ends of all the bifurcated branch vessels on the main vessel where the first bifurcation kernel is located;

calculate the reference lumen area of the proximal end of the distal main vessel connected to any bifurcation kernel one by one from near to far by means of the reference lumen area of the proximal main vessel of any bifurcation kernel and the reference lumen area of the proximal end of the branch vessel according to a distance between any bifurcation kernel on the main vessel where the first bifurcation kernel is located and the coronary artery vessel ostia; and if the proximal main vessel of the first bifurcation kernel closest to the coronary artery vessel ostia does not have a non-diseased lumen, determine whether the proximal end of the most distal vessel is diseased;

if no, directly acquire the reference lumen area of the proximal end of the most distal vessel according to the image information; and the reference lumen area of the proximal main vessel connected to any bifurcation kernel is calculated one by one from far to near by means of the reference lumen areas of the proximal end of the distal main vessel and the proximal end of the branch vessel of any bifurcation kernel according to a distance between the bifurcation kernel and the coronary artery vessel ostia.

Further, the coronary artery geometrical feature analysis module is configured to acquire a reference lumen area of a region of interest in the coronary artery vessel, including: acquiring a tunica media inner-circumference area S' of the region of interest in the coronary artery vessel, and the reference lumen area S=A*S' of a corresponding region, wherein 0.7≤A<1.

Further, the coronary geometrical feature analysis module acquires the image information of the coronary artery by means of non-invasive coronary artery CT radiography.

Further, the present invention provides an apparatus for acquiring a blood flow velocity of a coronary artery, including:

any one of the previously described apparatuses for acquiring the blood flow volume of the coronary artery, configured to acquire a blood flow volume at the coronary artery ostia; and a blood flow velocity calculation module, configured to obtain a blood flow velocity at the coronary artery ostia by dividing the blood flow volume at the coronary artery ostia by the reference lumen area at the ostia.

Further, the blood flow velocity calculation module is configured to calculate the blood flow velocity of any vascular segment in the coronary artery other than the coronary artery ostia stage by stage by means of the following formula 3 or formula 4 after the blood flow velocity at the coronary artery ostia is obtained:

$$v_1 = v_0 \left(1 - e^{r\frac{a_1 L_1}{a_2 L_2}}\right)$$ Formula 3

$v_0$ is the blood flow velocity of the proximal main vessel of the bifurcation kernel, and $v_1$ is the blood flow velocity of the distal main vessel of the bifurcation kernel;

$$v_2 = v_0 \left(1 - e^{r\frac{a_1 L_1}{a_2 L_2}}\right)$$ Formula 4

$v_2$ is the blood flow velocity of the branch vessel of the bifurcation kernel. Further, the present invention further provides another apparatus for acquiring a blood flow volume of a coronary artery, including:

a processor, a memory, and a computer-executable instruction stored in the memory.

The processor, when executing the computer-executable instruction, implements any one of the previously described methods for acquiring the blood flow volume of the coronary artery.

Further, the present invention provides an apparatus for acquiring a blood flow velocity of a coronary artery, including:

a processor, a memory, and a computer-executable instruction stored in the memory. The processor, when executing the computer-executable instruction, implements any one of the previously described methods for acquiring the blood flow velocity of the coronary artery.

In conclusion, a novel method for calculating the blood flow volume is provided. Without an additional trauma, firstly, the normal reference lumen is calculated based on a coronary bifurcation model in case of no coronary stenosis; secondly, the total blood flow volume at the coronary artery ostia is calculated based on the size of the reference lumen of the coronary artery; and finally, the blood flow distribution of the entire coronary artery tree is calculated based on the blood flow distribution ratio of the bifurcation model. The blood flow volume is directly estimated from the structural size of the coronary artery to obtain the blood flow distribution of the various vascular segments in the entire coronary artery tree, which can provide a more accurate boundary condition for image-based hemodynamic calculation.

SPECIFIC EMBODIMENTS

Embodiments 1 to 7 and Comparative Examples 1 to 2

A non-diseased coronary artery sample at the coronary artery ostia was selected;
a left coronary artery tree was segmented according to a CT coronary angiography image to obtain original geometrical feature data of the coronary artery, and geometrical feature data of a reference lumen of the non-diseased coronary artery was obtained by reconstruction by a method from near to far, wherein r=−1;
the volume of the reference lumen of the left coronary artery tree was calculated to be 1100 mm³;
a blood flow volume at the coronary artery ostia was calculated according to a formula $$Q = K * V^{\frac{3}{4}}, \quad\quad 1$$

and the value range of K was seen in Table 2; and
an area at the left coronary artery ostia was measured to be 11.5 mm², and a blood flow velocity was calculated according to the formula: blood flow velocity=blood flow volume/lumen area.

TABLE 1

|  | K | Q (mm³/s) | v (m/s) | Error |
|---|---|---|---|---|
| Embodiment 1 | 5 | 955.02 | 0.08 | −33% |
| Embodiment 2 | 6 | 1146.03 | 0.10 | −17% |
| Embodiment 3 | 6.5 | 1241.53 | 0.11 | −8% |
| Embodiment 4 | 7 | 1337.03 | 0.12 | 0% |
| Embodiment 5 | 8 | 1528.04 | 0.13 | 8% |
| Embodiment 6 | 9 | 1719.04 | 0.15 | 25% |
| Embodiment 7 | 9.5 | 1814.55 | 0.16 | 33% |
| Comparative example 1 | 10 | 1910.05 | 0.17 | 42% |
| Comparative example 2 | 4.5 | 859.52 | 0.07 | −42% |
| Comparative example 3 | — | — | 0.12 | — |

*An error is (the blood flow velocity v obtained in each embodiment or comparative example-the blood flow velocity v obtained in Comparative example 3)/the blood flow velocity v obtained in Comparative example 3.

Comparative example 3 (the blood flow velocity is calculated by a coronary angiography-based TIMI frame count method)

A target vascular segment was selected from a coronary angiography image, and its length was measured to be 80.26 mm; and a contrast agent needs 10 frames from the proximal end to the distal end of the vascular segment according to the angiography-based TIMI frame count method, and a coronary angiography taken frame frequency was 15 frames per second, so that the time was calculated to be 0.67 seconds.

Therefore, the blood flow velocity calculated by means of coronary angiography was: 80.26 mm/0.67 s=119.8 mm/s=0.12 m/s.

It can be seen from Table 1 that compared with the blood flow velocity calculated by the TIMI frame count method (the gold standard in the industry) in Comparative example 3, the blood flow volumes and the blood flow velocities obtained by the method provided by the present invention are close and have relatively small errors. Particularly in Embodiment 4, in case of K=7, the blood flow velocity of the coronary artery calculated by non-invasive CT coronary angiography is consistent with the result measured by the coronary angiography TIMI frame count method. In Comparative example 1 or 2, there is a relatively large error when K is greater than 9.5 or smaller than 5.

It can be seen that the method for obtaining the blood flow volume of the coronary artery provided by the present invention directly estimates the blood flow from the structural size of the coronary artery, without segmenting the CT image to obtain the cardiac muscle first. Since in existing radiography-based hemodynamic calculation, segmentation of the coronary artery is necessary, the estimation of the blood flow volume by the size of the coronary artery will not increase the workload of image processing. Compared with estimation of the blood flow volume of the coronary artery by the size of the cardiac muscle of a patient in the prior art, this method is simpler and more accurate.

In summary, the above-mentioned embodiments provided by the present invention are merely illustrative of the principle and effects of the present invention, and are not used to limit the present invention. Anyone familiar with this technology can modify or change the above-mentioned embodiments without departing from the spirit and scope of the present invention. Therefore, all equivalent modifications or changes made by those of ordinary skill in the art without departing from the spirit and technical ideas disclosed by the present invention shall still be covered by the claims of the present invention.

The invention claimed is:

1. A method for acquiring a blood flow volume of a coronary artery, comprising:
   acquiring image information of a coronary artery to obtain geometrical feature data of the coronary artery;
   obtaining, according to the geometrical feature data of the coronary artery, the total volume V of a reference lumen of the coronary artery; and
   calculating a blood flow volume Q at coronary artery ostia according to a formula 1:

$$Q = K * V^{\frac{3}{4}} \qquad \text{Formula 1}$$

wherein when the unit of Q is mm$^3$/s, and when the unit of V is mm$^3$, a value range of K is 5-9.5, preferably 6.5-8, and most preferably 7, and the image information of the coronary artery is image information of a coronary artery with stenosis.

2. The method for acquiring the blood flow volume of the coronary artery according to claim 1, wherein
   the total volume V of the reference lumen of the coronary artery is obtained by means of the following steps:
   the geometrical feature data of the coronary artery comprising a length of a coronary artery vessel and a reference lumen area of the coronary artery vessel,
   cutting the coronary artery vessel along a center line of the vessel into a plurality of sheets perpendicular to the center line of the vessel, defining a bottom area of each sheet as a reference lumen area of the corresponding part, and summing the volumes of the plurality of sheets to obtain the total volume V of the reference lumen of the coronary artery in combination with the length of the coronary artery vessel.

3. The method for acquiring the blood flow volume of the coronary artery according to claim 2, wherein
   a reference lumen area of a region of interest in the coronary artery vessel is obtained by the following method:
   the geometrical feature data of the coronary artery comprises a tunica media inner-circumference area S' of the region of interest in the coronary artery vessel, and
   the reference lumen area S=A*S' of a corresponding region, wherein 0.7≤A<1.

4. The method for acquiring the blood flow volume of the coronary artery according to claim 1, wherein
   the total volume V of the reference lumen of the coronary artery is obtained by means of the following steps:
   recognizing bifurcation kernels of the coronary artery according to the geometrical feature data of the coronary artery; and
   the coronary artery comprising a plurality of bifurcation kernels and a plurality of vascular segments segmented by the bifurcation kernels, summing the volumes of the plurality of bifurcation kernels and the plurality of vascular segments to obtain the total volume V of the reference lumen of the coronary artery.

5. The method for acquiring the blood flow volume of the coronary artery according to claim 4, wherein
   each bifurcation kernel is simplified into a circular truncated cone to calculate the volume; an area of one bottom surface of the circular truncated cone is a reference lumen area of a proximal end of the bifurcation kernel, and an area of the other bottom surface of the circular truncated cone is a sum of reference lumen areas of two distal ends of the bifurcation kernel; and a height of the circular truncated cone is a distance from the center of the proximal end of the bifurcation kernel to a bifurcation ridge.

6. The method for acquiring the blood flow volume of the coronary artery according to claim 4, wherein the plurality of vascular segments are simplified into circular truncated cones to calculate volumes; areas of the top and bottom surfaces of each circular truncated cone are respectively a reference lumen area of a proximal end of the corresponding vascular segment and a reference lumen area of a distal end of the corresponding vascular segment; and a height of each circular truncated cone is a length of a center line of the corresponding vascular segment.

7. The method for acquiring the blood flow volume of the coronary artery according to claim 4, wherein the plurality of vascular segments comprise the most distal vascular segment and other vascular segments other than the most distal vascular segment;
   the other vascular segments other than the most distal vascular segment are simplified into cylinders to calculate volumes; a bottom area of each cylinder is a reference lumen area of any part of the vascular segment, and a height of the cylinder is a length of a center line of the vascular segment.

8. The method for acquiring the blood flow volume of the coronary artery according to claim 7, wherein the geometrical feature data comprises a bifurcation angle $\alpha_1$ between a proximal main vessel and a distal main vessel of any bifurcation kernel, a full length $L_1$ of the distal main vessel, a bifurcation angle $\alpha_2$ between the proximal main vessel and a branch vessel, a full length $L_2$ of the branch vessel, and any two of a reference lumen area $S_0$ of the proximal main vessel of any bifurcation kernel, a reference lumen area $S_1$ of the proximal end of the distal main vessel of the bifurcation kernel, and a reference lumen area $S_2$ of the proximal end of the branch vessel of the bifurcation kernel; and one remaining reference lumen area is obtained by means of the following formula 2:

$$S_0 = \left(1 - e^{r\frac{\alpha_1 L_1}{\alpha_2 L_2}}\right) S_1 + \left(1 - e^{r\frac{\alpha_2 L_2}{\alpha_1 L_1}}\right) S_2 \qquad \text{Formula 2}$$

wherein e is a natural constant, and $-\infty \leq r < -0.6$, preferably $-2 \leq r < -0.75$, and more preferably $r=-1$.

9. The method for acquiring the blood flow volume of the coronary artery according to claim 8, wherein whether a proximal main vessel of a first bifurcation kernel closest to coronary artery vessel ostia has a non-diseased lumen is determined;

if yes, the reference lumen area of the proximal main vessel of the first bifurcation kernel is defined as a reference lumen area of any non-diseased part of the proximal main vessel of the first bifurcation kernel;

all branch vessels on the main vessel where the first bifurcation kernel is located are considered to be not diseased by default, and the reference lumen areas of the proximal ends of all the bifurcated branch vessels on the main vessel where the first bifurcation kernel is located are directly acquired according to the image information;

the reference lumen area of the proximal end of the distal main vessel connected to any bifurcation kernel is calculated one by one from near to far by means of the reference lumen area of the proximal main vessel of any bifurcation kernel and the reference lumen area of the proximal end of the branch vessel according to a distance between any bifurcation kernel on the main vessel where the first bifurcation kernel is located and the coronary artery vessel ostia;

if the proximal main vessel of the first bifurcation kernel closest to the coronary artery vessel ostia does not have a non-diseased lumen, whether the proximal end of the most distal vessel is diseased is determined;

if no, the reference lumen area of the proximal end of the most distal vessel is directly acquired according to the image information; and the reference lumen area of the proximal main vessel connected to any bifurcation kernel is calculated one by one from far to near by means of the reference lumen of the proximal end of the distal main vessel and the proximal end of the branch vessel of any bifurcation kernel according to a distance between the bifurcation kernel and the coronary artery vessel ostia.

10. The method for acquiring the blood flow volume of the coronary artery according to claim 1, wherein the image information of the coronary artery is acquired by means of non-invasive coronary artery CT radiography.

11. A method for acquiring a blood flow velocity of a coronary artery, wherein the blood flow velocity at coronary artery ostia is obtained by dividing the blood flow volume at coronary artery ostia, obtained according to claim 1, by the reference lumen area at the ostia.

12. The method for acquiring the blood flow velocity of the coronary artery according to claim 11, wherein the blood flow velocity of any vascular segment in the coronary artery other than the coronary artery ostia is calculated stage by stage by means of the following formula 3 or formula 4 after the blood flow velocity at the coronary artery ostia is obtained:

$$v_1 = v_0\left(1 - e^{r\frac{\alpha_1 L_1}{\alpha_2 L_2}}\right) \qquad \text{Formula 3}$$

$v_0$ is a blood flow velocity of a proximal main vessel of each bifurcation kernel, and $v_1$ is a blood flow velocity of a distal main vessel of the bifurcation kernel;

$$v_2 = v_0\left(1 - e^{r\frac{\alpha_2 L_2}{\alpha_1 L_1}}\right) \qquad \text{Formula 4}$$

$v_2$ is a blood flow velocity of a branch vessel of each bifurcation kernel.

13. An apparatus for acquiring a blood flow velocity of a coronary artery, comprising:

a processor, a memory, and a computer-executable instruction stored in the memory, wherein the processor, when executing the computer-executable instruction, implements the method for acquiring the blood flow velocity of the coronary artery according to claim 11.

14. An apparatus for acquiring a blood flow volume of a coronary artery, comprising:

a processor, a memory, and a computer-executable instruction stored in the memory, wherein the processor, when executing the computer-executable instruction, implements the method for acquiring the blood flow volume of the coronary artery according to claim 1.

15. An apparatus for acquiring a blood flow volume of a coronary artery, comprising:

a coronary artery geometrical feature analysis module, configured to acquire image information of a coronary artery to obtain geometrical feature data of the coronary artery;

a volume calculation module, configured to obtain the total volume V of a reference lumen of the coronary artery according to the geometrical feature data of the coronary artery; and a blood flow volume calculation module, configured to calculate a blood flow volume Q at coronary artery ostia according to a formula 1:

$$Q = K * V^{\frac{3}{4}} \qquad \text{Formula 1}$$

wherein when the unit of Q is mm$^3$/s, and when the unit of V is mm$^3$, a value range of K is 5-9.5, preferably 6.5-8, and most preferably 7.

16. The apparatus for acquiring the blood flow volume of the coronary artery according to claim 15, wherein
the coronary artery geometrical feature analysis module is configured to acquire a length of a coronary artery vessel and a reference lumen area of the coronary artery vessel;
the volume calculation module is configured to cut the coronary artery vessel along a center line of the vessel into a plurality of sheets perpendicular to the center line of the vessel, define a bottom area of each sheet as a reference lumen area of the corresponding part, and sum the volumes of the plurality of sheets to obtain the total volume V of the reference lumen of the coronary artery in combination with the length of the coronary artery vessel.

17. The apparatus for acquiring the blood flow volume of the coronary artery according to claim 16, wherein
the coronary artery geometrical feature analysis module is configured to acquire a reference lumen area of a region of interest in the coronary artery vessel, comprising:
acquiring a tunica media inner-circumference area S' of the region of interest in the coronary artery vessel, and
the reference lumen area S=A*S' of a corresponding region, wherein $0.7 \leq A < 1$.

18. The apparatus for acquiring the blood flow volume of the coronary artery according to claim 15, wherein
the volume calculation module is configured to
recognize bifurcation kernels of the coronary artery according to the geometrical feature data of the coronary artery; and
the coronary artery comprising a plurality of bifurcation kernels and a plurality of vascular segments segmented by the bifurcation kernels, sum the volumes of the plurality of bifurcation kernels and the plurality of vascular segments to obtain the total volume V of the reference lumen of the coronary artery.

19. The apparatus for acquiring the blood flow volume of the coronary artery according to claim 18, wherein
the volume calculation module is configured to simplify each bifurcation kernel into a circular truncated cone to calculate the volume; an area of one bottom surface of the circular truncated cone is a reference lumen area of a proximal end of the bifurcation kernel, and an area of the other bottom surface of the circular truncated cone is a sum of reference lumen areas of two distal ends of the bifurcation kernel; and a height of the circular truncated cone is a distance from the center of the proximal end of the bifurcation kernel to a bifurcation ridge.

20. The apparatus for acquiring the blood flow volume of the coronary artery according to claim 18, wherein the volume calculation module is configured to simplify the plurality of vascular segments into circular truncated cones to calculate volumes; areas of the top and bottom surfaces of each circular truncated cone are respectively a reference lumen area of a proximal end of the corresponding vascular segment and a reference lumen area of a distal end of the corresponding vascular segment; and a height of each circular truncated cone is a length of a center line of the corresponding vascular segment.

21. The apparatus for acquiring the blood flow volume of the coronary artery according to claim 18, wherein the plurality of vascular segments comprise the most distal vascular segment and other vascular segments other than the most distal vascular segment;
the volume calculation module is configured to simplify the other vascular segments other than the most distal vascular segment into cylinders to calculate volumes; a bottom area of each cylinder is a reference lumen area of any part of the vascular segment; and a height of the cylinder is a length of a center line of the vascular segment.

22. The apparatus for acquiring the blood flow volume of the coronary artery according to claim 21, wherein
the coronary artery geometrical feature analysis module is configured to
acquire a bifurcation angle $\alpha_1$ between a proximal main vessel and a distal main vessel of any bifurcation kernel, a full length $L_1$ of the distal main vessel, a bifurcation angle $\alpha_2$ between the proximal main vessel and a branch vessel, a full length $L_2$ of the branch vessel,
and any two of a reference lumen area $S_0$ of the proximal main vessel of any bifurcation kernel, a reference lumen area $S_1$ of the proximal end of the distal main vessel of the bifurcation kernel, and a reference lumen area $S_2$ of the proximal end of the branch vessel of the bifurcation kernel; and
obtain one remaining reference lumen area by means of the following formula 2:

$$S_0 = \left(1 - e^{r\frac{\alpha_1 L_1}{\alpha_2 L_2}}\right)S_1 + \left(1 - e^{r\frac{\alpha_2 L_2}{\alpha_1 L_1}}\right)S_2 \quad \text{Formula 2}$$

wherein e is a natural constant; and $-\infty \leq r < -0.6$, preferably $-2 \leq r < -0.75$, and most preferably $r=-1$.

23. The apparatus for acquiring the blood flow volume of the coronary artery according to claim 22, wherein
the coronary artery geometrical feature analysis module is configured to
determine whether a proximal main vessel of a first bifurcation kernel closest to coronary artery vessel ostia has a non-diseased lumen;
if yes, define the reference lumen area of the proximal main vessel of the first bifurcation kernel as a reference lumen area of any non-diseased part of the proximal main vessel of the first bifurcation kernel;
consider all branch vessels on the main vessel where the first bifurcation kernel is located to be not diseased by default, and directly acquire, according to the image information, the reference lumen areas of the proximal ends of all the bifurcated branch vessels on the main vessel where the first bifurcation kernel is located;
calculate the reference lumen area of the proximal end of the distal main vessel connected to any bifurcation kernel one by one from near to far by means of the reference lumen area of the proximal main vessel of any bifurcation kernel and the reference lumen area of the proximal end of the branch vessel according to a distance between any bifurcation kernel on the main vessel where the first bifurcation kernel is located and the coronary artery vessel ostia; and
if the proximal main vessel of the first bifurcation kernel closest to the coronary artery vessel ostia does not have a non-diseased lumen,
determine whether the proximal end of the most distal vessel is diseased;

if no, directly acquire the reference lumen area of the proximal end of the most distal vessel according to the image information; and calculate the reference lumen area of the proximal main vessel connected to any bifurcation kernel one by one from far to near by means of the reference lumen of the proximal end of the distal main vessel and the proximal end of the branch vessel of any bifurcation kernel according to a distance between the bifurcation kernel and the coronary artery vessel ostia.

24. The apparatus for acquiring the blood flow volume of the coronary artery according to claim 15, wherein the coronary artery geometrical feature analysis module acquires the image information of the coronary artery by means of non-invasive coronary artery CT radiography.

25. An apparatus for acquiring a blood flow velocity of a coronary artery, comprising:

the apparatus for acquiring the blood flow volume of the coronary artery according to claim 15, configured to acquire a blood flow volume at coronary artery ostia; and a blood flow velocity calculation module, configured to obtain a blood flow velocity at the coronary artery ostia by dividing the blood flow volume at the coronary artery ostia by the reference lumen area at the ostia.

26. The apparatus for acquiring the blood flow velocity of the coronary artery according to claim 25, wherein the blood flow velocity calculation module is configured to calculate the blood flow velocity of any vascular segment in the coronary artery other than the coronary artery ostia stage by stage by means of the following formula 3 or formula 4 after the blood flow velocity at the coronary artery ostia is obtained:

$$v_1 = v_0\left(1 - e^{r\frac{\alpha_1 L_1}{\alpha_2 L_2}}\right) \quad \text{Formula 3}$$

$v_0$ is a blood flow velocity of a proximal main vessel of each bifurcation kernel, and $v_1$ is a blood flow velocity of a distal main vessel of the bifurcation kernel;

$$v_2 = v_0\left(1 - e^{r\frac{\alpha_2 L_2}{\alpha_1 L_1}}\right) \quad \text{Formula 4}$$

$v_2$ is a blood flow velocity of a branch vessel of each bifurcation kernel.

\* \* \* \* \*